(12) United States Patent
Ng et al.

(10) Patent No.: US 9,107,940 B2
(45) Date of Patent: *Aug. 18, 2015

(54) COMPOSITIONS AND METHODS FOR TREATING AND PREVENTING SKELETAL MUSCLE DEFICIENCIES

(71) Applicants: The Regents of the University of Michigan, Ann Arbor, MI (US); Phrixus Pharmaceuticals, Inc., Ann Arbor, MI (US)

(72) Inventors: Rainer Ng, Seattle, WA (US); Joseph M. Metzger, St. Paul, MN (US); Lorraine Reeve, Dexter, MI (US); Bruce Markham, Novi, MI (US)

(73) Assignees: The Regents of the University of Michigan, Ann Arbor, MI (US); Phrixus Pharmaceuticals, Inc., Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/508,599

(22) Filed: Oct. 7, 2014

(65) Prior Publication Data

US 2015/0030559 A1  Jan. 29, 2015

Related U.S. Application Data

(62) Division of application No. 12/747,073, filed as application No. PCT/US2008/087185 on Dec. 17, 2008, now Pat. No. 8,852,568.

(60) Provisional application No. 61/014,304, filed on Dec. 17, 2007.

(51) Int. Cl.
*A61K 31/765* (2006.01)
*A61K 45/06* (2006.01)

(52) U.S. Cl.
CPC .............. *A61K 31/765* (2013.01); *A61K 45/06* (2013.01)

(58) Field of Classification Search
CPC .............................. A61K 31/765; A61K 45/06
See application file for complete search history.

(56) References Cited

U.S. PATENT DOCUMENTS

| | | |
|---|---|---|
| 5,605,687 A | 2/1997 | Lee |
| 5,733,572 A | 3/1998 | Unger et al. |
| 6,747,064 B2 | 6/2004 | Emanuele et al. |
| 6,761,824 B2 | 7/2004 | Reeve et al. |
| 6,977,045 B2 | 12/2005 | Reeve et al. |
| 2003/0124190 A1 | 7/2003 | Williams et al. |
| 2004/0253277 A1 | 12/2004 | Meadows et al. |
| 2004/0265388 A1 | 12/2004 | Zhang et al. |
| 2006/0121016 A1 | 6/2006 | Lee ........................ 424/94.1 |
| 2007/0237740 A1 | 10/2007 | Reddington |
| 2011/0044935 A1 | 2/2011 | Metzger et al. |

FOREIGN PATENT DOCUMENTS

| | | | | |
|---|---|---|---|---|
| CA | WO2006/091941 | * | 8/2006 | ............ A61K 31/74 |
| JP | 2008-531598 | | 8/2008 | |
| JP | 2009-525302 | | 7/2009 | |
| WO | 2006/091941 | | 8/2006 | |
| WO | WO2006/091941 | | 8/2006 | ............ A61K 31/77 |
| WO | 2006/100017 | | 9/2006 | |
| WO | 2007/088123 | | 8/2007 | |
| WO | 2011/066201 | | 6/2011 | |

OTHER PUBLICATIONS

Markham Declaration, U.S. Appl. No. 12/747,037 (Dec. 19, 2012).*
Helmut Drexler, et al, Alterations of Skeletal Muscle in Chronic Heart Failure, 85 Circulation 1751 (1992).*
Volker Straub & Kevin Campbell, Muscular Dystrophies and the Dystrophin-Glycoprotein Complex, 10 Curr. Opin. Neurol. 168 (1997).*
Beaton, L., et al., "Contraction-induced muscle damage in humans following calcium channel blocker administration", Journal of Physiology (2002), 544.3, pp. 849-859.
Brooks, Susan V., "Rapid recovery following contraction-induced injury to in situ skeletal muscles in mdx mice", Journal of Muscle Research and Cell Mobility 19, pp. 179-187 (1998).
International Search Report for PCT/US2008/087185 dated Jul. 29, 2009.
International Search Report for PCT/US2010/057560, dated Aug. 2, 2011.
NG, Rainer, et al., "Poloxamer 188 reduces the contraction-induced force decline in lumbrical muscles from mdx mice", Am. J. Physiol. Cell Physiol 295: C146-C150, 2008.
Quinlan, John G., et al., "Poloxamer 188 failed to prevent exercise-induced membrane breakdown in mdx skeletal muscle fibers", Neuromuscular Disorders, 2006, vol. 16, pp. 856-864.
Straub, Volker, et al., "Muscular dystrophies and the dystrophin-glycoprotein complex", Current Opinion in Neurology, 1997, vol. 10, pp. 168-175.
English translation of JP Office Action mailed Oct. 29, 2013 from JP Patent Application No. 2010-539736.
Petrof, Basil J., "The molecular basis of activity-induced muscle injury in Duchenne muscular dystrophy," Molecular and Cellular Biochemistry 179:111-123 (1998).
English translation of Japanese Office Action mailed Jan. 22, 2013 from JP Patent Application No. 2010-539736.
Whitehead, Nicholas P., et al., "Streptomycin reduces stretch-induced membrane permeability in muscles from mdx mice," Neuromuscul Disord 2006, vol. 16, pp. 845-854.

(Continued)

*Primary Examiner* — Sean Basquill
(74) *Attorney, Agent, or Firm* — Casimir Jones, S.C.

(57) ABSTRACT

The present invention relates to compositions and methods for treating and preventing skeletal muscle deficiencies. In particular, the present invention provides compositions comprising poloxamers (e.g., poloxamer 188-P188) and methods of using the same for treating and preventing skeletal muscle deficiencies and injuries (e.g., dystrophin-deficient skeletal muscle; skeletal muscle having a contraction force deficit; skeletal muscle having a $Ca^{2+}$ imbalance; skeletal muscle having microtears).

13 Claims, 4 Drawing Sheets

(56) References Cited

OTHER PUBLICATIONS

Steinhard, Richard A., "Rips Repaired," Nature 2005, vol. 436, p. 925.
Townsend, DeWayne, et al., "Cardiomyopathy of Duchenne muscular dystrophy: pathogenesis and prospect of membrane sealants as a new therapeutic approach," Expert Rev Cardiovasc Ther, Jan. 2007, vol. 5, pp. 99-109.
H.G. Radley, et al, Duchenne Muscular Dystrophy: Focus on Pharmaceutical and Nutritional Intervention, 39 Intl. J Biochem. Cell Bio. 469 (Oct. 10, 2006).
Collins et al., 2007, "Structural and functional recovery of electropermeabilized skeletal muscle in-vivo after treatment with surfactant poloxamer 188", Biochimica Et Biophysica Acta, vol. 1768, No. 5, pp. 1238-1246.
Scheuerbrandt et al., 2006, "Approaching therapies for boys with Duchenne muscular dystrophy. Parent Project Muscular Dystrophy. Annual Conference in Cincinnati/Ohio, Jul. 13-16, 2006", Acta Myologica, vol. 25, No. 2, pp. 77-97.
Ryall James et al., 2007, "The membrane sealant poloxamer reduces membrane permeability in tibialis anterior muscles from dystrophic mdx mice", FASEB Journal, vol. 21, No. 6, A945.
European Search Report dated Mar. 11, 2011 from EP Application No. 08861170.2.
Adams-Graves et al., "RheothRx (poloxamer 188) injection for the acute painful episode of sickle cell disease: a pilot study", 1997, Blood, 90:2041-2046.
Blake, "Function and genetics of dystrophin and dystrophin-related proteins in muscle", 2002, Physiol Rev 82:291-329.
Borgens et al., "Subcutaneous tri-block copolymer produces recovery from spinal cord injury", 2004, J Neurosci Res, 76:141-154.
Bulfield et al., "X chromosome-linked muscular dystrophy (mdx) in the mouse", 1984, Proc Natl Acad Sci USA, 81:1189-1192.
Chareonithaitawee et al., "The impact of time to thrombolytic treatment on outcome in patients with acute myocardial infarction. For the CORE investigators (Collaborative Organisation for RheothRx Evaluation)", 2000, Heart, 84:142-148.
Emanuele et al., "FLOCOR: a new anti-adhesive, rheologic agent", 1998, Expert Opin Investic Drugs, 7:1193-1200.
Gibbs and Hagemann, "Purified poloxamer 188 for sickle cell vaso-occlusive crisis", 2004, Ann Pharmacother, 38:320-324.
Goyenvalle et al., "Rescue of dystrophic muscle through U7 snRNA-mediated exon skipping", 2004, Science, 306:1796-9.
Gregorevic et al., "Systemic delivery of genes to striated muscles using adeno-associated viral vectors", 2004, Nat Med, 10:828-34.
Grover et al., "Effect of a nonionic surface-active agent on blood viscosity and platelet adhesiveness", 1969, Circulation, 39(5 Suppl 1):I249-52.
Head et al., "Abnormalities in structure and function of limb skeletal muscle fibres of dystrophic mdx mice", 1992, Proc Biol Sci, 248:163-169.
Hoffman et al., "Dystrophin: the protein product of the Duchenne muscular dystrophy locus", 1987, Cell, 51:919-928.
Kabanov et al., "Pluronic block copolymers for overcoming drug resistance in cancer", 2002, Adv Drug Deliv Rev, 54:759-779.
Kaprielian and Severs, "Dystrophin and the cardiomyocyte membrane cytoskeleton in the healthy and failing heart", 2000, Heart Failure Reviews, 5:221-238.
Lamb et al., "Raised intracellular [Ca2+] abolishes excitation-contraction coupling in skeletal muscle fibres of rat and toad", 1995, J Physiol, 489 (Pt 2):349-62.
Lee et al., "Surfactant-induced sealing of electropermeabilized skeletal muscle membranes in vivo", 1992, Proc Natl Acad Sci USA, 89:4524-4528.
Li et al., "A highly functional mini-dystrophin/GFP fusion gene for cell and gene therapy studies of Duchenne muscular dystrophy", 2006, Hum Mol Genet, 15:1610-1622.
Lynch et al., "Force and power output of fast and slow skeletal muscles from mdx mice 6-28 months old", 2001, J Physiol, 535:591-600.
Marks et al., "Amphiphilic, tri-block copolymers provide potent membrane-targeted neuroprotection", 2001, FASEB J, 15:1107-1109.
Maskarinec et al., "Direct observation of poloxamer 188 insertion into lipid monolayers", 2002, Biophys J, 82:1453-1459.
Merchant et al., "Poloxamer 188 enhances functional recovery of lethally heat-shocked fibroblasts", 1998, J Surg Res, 74:131-140.
O'Keefe et al., "Poloxamer-188 as an adjunct to primary percutaneous transluminal coronary angioplasty for acute myocardial infarction", 1996, Am J Cardiol, 78:747-750.
Ohlendieck and Campbell, "Dystrophin-associated proteins are greatly reduced in skeletal muscle from mdx mice", 1991, J Cell Biol, 115:1685-1694.
Petrof, "Molecular pathophysiology of myofiber injury in deficiencies of the dystrophin-glycoprotein complex", 2002, Am J Phys Med Rehabil, 81:S162-S174.
Reeve, 1997, In: Handbook of Biodegradable Polymers, Harwood Academic Pub, 231-249.
Schaer et al., "Beneficial effects of RheothRx injection in patients receiving thrombolytic therapy for acute myocardial infarction. Results of a randomized, double-blind, placebo-controlled trial", 1996, Circulation 94:298-307.
Schmolka, "A Review of Block Polymer Surfactants", 1977, J Am Oil Chem Soc, 54:110-116.
Sokabe et al., "Blockers and activators for stretch-activated ion channels of chick skeletal muscle", 1993, Ann NY Acad Sci, 707:417-420.
Squire et al., "Prevention of pathology in mdx mice by expression of utrophin: analysis using an inducible transgenic expression system", 2002, Hum Mol Genet, 11:3333-44.
Torrente et al., "Human circulating AC133(+) stem cells restore dystrophin expression and ameliorate function in dystrophic skeletal muscle", 2004, J Clin Invest, 114:182-95.
Vandebrouck et al., "Involvement of TRPC in the abnormal calcium influx observed in dystrophic (mdx) mouse skeletal muscle fibers", 2002, J Cell Biol, 158:1089-1096.
Verburg et al., "Disruption of excitation-contraction coupling and titin by endogenous Ca2+-activated proteases in toad muscle fibres", 2005, J Physiol 564:775-790.
Yasuda et al., "Dystrophic heart failure blocked by membrane sealant poloxamer", 2005, Nature, 436:1025-1029.
Yeung et al., "Effects of stretch-activated channel blockers on [Ca2+]i and muscle damage in the mdx mouse", 2005, J Physiol, 562:367-380.

\* cited by examiner

| Copolymer | MW[a] | Average no. of EO units (x)[b] | Average no. of PO units (y)[b] | HLB[c] | Cloud point in 1% aqueous solution (°C)[c] | CMC (M)[d] |
|---|---|---|---|---|---|---|
| L35 | 1900 | 21.59 | 16.36 | 19 | 73 | 5.3×10⁻³ |
| L43 | 1850 | 12.61 | 22.33 | 12 | 42 | 2.2×10⁻³ |
| L44 | 2200 | 20.00 | 22.76 | 16 | 65 | 3.6×10⁻³ |
| L61 | 2000 | 4.55 | 31.03 | 3 | 24 | 1.1×10⁻⁴ |
| L62 | 2500 | 11.36 | 34.48 | 7 | 32 | 4.0×10⁻⁵ |
| L64 | 2900 | 26.36 | 30.00 | 15 | 58 | 4.8×10⁻⁵ |
| F68 | 8400 | 152.73 | 28.97 | 29 | >100 | 4.8×10⁻⁵ |
| L81 | 2750 | 6.25 | 42.67 | 2 | 20 | 2.3×10⁻⁵ |
| P84 | 4200 | 38.18 | 43.45 | 14 | 74 | 2.1×10⁻⁵ |
| P85 | 4600 | 52.27 | 39.66 | 16 | 85 | 6.5×10⁻⁵ |
| F87 | 7700 | 122.50 | 39.83 | 24 | >100 | 9.1×10⁻⁵ |
| F88 | 11400 | 207.27 | 39.31 | 28 | >100 | 2.5×10⁻⁵ |
| L92 | 3650 | 18.59 | 50.34 | 6 | 26 | 3.8×10⁻⁵ |
| F98 | 13000 | 236.36 | 44.83 | 28 | >100 | 7.7×10⁻⁷ |
| L101 | 3800 | 8.64 | 58.97 | 1 | 15 | 3.1×10⁻⁶ |
| P103 | 4950 | 33.75 | 59.74 | 9 | 86 | 6.1×10⁻⁶ |
| P104 | 5900 | 53.64 | 61.03 | 13 | 81 | 3.4×10⁻⁶ |
| P105 | 6500 | 73.86 | 56.03 | 15 | 91 | 6.2×10⁻⁶ |
| F108 | 14600 | 265.45 | 50.34 | 27 | >100 | 2.2×10⁻⁷ |
| L121 | 4400 | 10.00 | 68.28 | 1 | 14 | 1.0×10⁻⁶ |
| P123 | 5750 | 39.20 | 69.40 | 8 | 90 | 4.4×10⁻⁶ |
| P127 | 12600 | 200.45 | 65.17 | 22 | >100 | 2.8×10⁻⁶ | a The average molecular weights provided by the manufacturer (BASF, Wyandotte, MI).
    b The average numbers of EO and PO units were calculated using the average molecular weights.
    c HLB values of the copolymers; the cloud points were determined by the manufacturer.
    d Critical micellization concentration values were determined previously using pyrene probe (See, e.g., Kozlov et al., Macromolecules 33 (2000) 3305–3313).

COMPOSITIONS AND METHODS FOR TREATING AND PREVENTING SKELETAL MUSCLE DEFICIENCIES

CROSS-REFERENCE TO RELATED APPLICATIONS

This application is a divisional of U.S. patent application Ser. No. 12/747,073, filed Oct. 22, 2010, now allowed as U.S. Pat. No. 8,852,568, which is a U.S. National Stage Entry of expired International Patent Application No. PCT/US2008/087185, International Filing Date Dec. 17, 2008, which claims the benefit of priority to expired U.S. Provisional Patent Application No. 61/014,304, filed Dec. 17, 2007, the contents of which are hereby incorporated by reference in their entireties.

STATEMENT REGARDING FEDERALLY SPONSORED RESEARCH OR DEVELOPMENT

This invention was made with government support under AG015434 and AG020591 awarded by the National Institutes of Health. The government has certain rights in the invention.

FIELD OF THE INVENTION

The present invention relates to compositions and methods for treating and preventing skeletal muscle deficiencies. In particular, the present invention provides compositions comprising poloxamers (e.g., poloxamer 188-P188) and methods of using the same for treating and preventing skeletal muscle deficiencies and injuries (e.g., dystrophin-deficient skeletal muscle; skeletal muscle having a contraction force deficit; skeletal muscle having a $Ca^{2+}$ imbalance; skeletal muscle having microtears).

BACKGROUND OF THE INVENTION

Duchenne Muscular Dystrophy (DMD) is an X-linked genetic disease caused by a mutation in the dystrophin gene. As a result, muscles from patients with DMD lack dystrophin, a 427 kDa protein located on the cytoplasmic surface of the plasma membrane, the sarcolemma, of muscle fibres (see, e.g., Blake D J, et al., (2002) Physiol Rev 82, 291-329). Dystrophin is required for the assembly of the dystrophin-associated glycoprotein complex that is embedded in the sarcolemma (see, e.g., Ohlendieck K & Campbell K P (1991) J Cell Biol 115, 1685-1694). The dystrophin-glycoprotein complex links the actin cytoskeleton to the basement membrane and is thought to provide mechanical stability to the sarcolemma (see, e.g., Petrof B J (2002) Am J Phys Med Rehabil 81, S162-S174). Although the exact function of dystrophin is still unknown, the pathology demonstrated by the skeletal muscles of young males that lack dystrophin is clear. Boys with DMD experience progressive muscle weakness beginning at about 2-5 years of age, are wheelchair bound by age 12, and die in their mid-twenties from respiratory, or cardiac failure (see, e.g., Hoffman E P, et al., (1987) Cell 51, 919-928).

There exists a need for new compositions and new methods for treating skeletal muscle disorders in general, as well as disorders related to dystrophic cells, tissues and subjects, and for preventing and/or correcting the underlying bases of pathogenesis in subjects with skeletal muscle disorders (e.g., generally as well as in dystrophic subjects).

SUMMARY OF THE INVENTION

The present invention relates to compositions and methods for treating and preventing skeletal muscle deficiencies. In particular, the present invention provides compositions comprising poloxamers (e.g., poloxamer 188-P188) and methods of using the same for treating and preventing skeletal muscle deficiencies and injuries (e.g., dystrophin-deficient skeletal muscle; skeletal muscle having a contraction force deficit; skeletal muscle having a $Ca^{2+}$ imbalance; skeletal muscle having microtears).

Experiments conducted during the course of development of embodiments for the present invention demonstrated that poloxamers were effective in reducing skeletal muscle deficiencies, including but not limited to, dystrophin-deficient skeletal muscle, skeletal muscle having a contraction force deficit, skeletal muscle having a $Ca^{2+}$ imbalance, and/or skeletal muscle having microtears.

Accordingly, in certain embodiments, the present invention provides methods for treating a subject with a skeletal muscle contraction force deficit comprising administering to the subject a composition comprising a poloxamer under conditions such that the skeletal muscle contraction force deficit is improved in the subject. In certain embodiments, the present invention provides methods for preventing skeletal muscle contraction force deficit in a dystrophin deficient subject comprising administering to the subject a composition comprising a poloxamer. In certain embodiments, the present invention provides methods for reducing calcium concentration in skeletal muscle comprising administering a composition comprising a poloxamer to the skeletal muscle.

The methods are not limited to a particular type of poloxamers. In some embodiments, the poloxamer is a purified or fractionated poloxamer. In some embodiments, the poloxamer is P188, P138, P237, P288, P124, P338, and/or P407. In some embodiments, poloxamines and/or polyglycidols are used instead of, or with, poloxamers. The methods are not limited to a particular type of subject. In some embodiments, the subject is a human subject. In some embodiments the subject is a non-human subject (e.g., a mouse). In some embodiments, the subject is a dystrophin deficient subject. In some embodiments, the subject has Duchene's muscular dystrophy. In some embodiments, the subject suffers from a skeletal muscle contraction force deficit. The methods are not limited to a particular form of administration of the composition. In some embodiments, the composition is administered via intravenous administration. In some embodiments, the administration is local (e.g., intramuscular). The methods are not limited to treating a particular type of skeletal muscle. Examples of skeletal muscle that may be treated with the methods of the present invention include, but are not limited to, gastrocnemius, tibialis posterior, soleus, longus, brevis, gluteus maximus muscle, biceps femoris, semitendinosus, semimembranosus, iliopsoas, quadriceps femoriss, adductor muscles of the hip, levator scapulae, trapezius, rectus abdominis, transversus abdominis, abdominal external oblique muscle, abdominal internal oblique muscle, erector spinae, pectoralis major, biceps brachii, triceps brachii, brachialis, pronator teres, brachioradialis, rhomboids, deltoid, latissimus dorsi, diaphragm, and rotator cuff.

The methods are not limited to a particular dosage level for poloxamer administration to a subject. In some embodiments, it is expected that each dose (e.g., of a composition comprising a poloxamer (e.g., administered to a subject to prevent or treat a skeletal muscle deficiency (e.g., dystrophin-deficient skeletal muscle; skeletal muscle having a contraction force deficit; skeletal muscle having a $Ca^{2+}$ imbalance; skeletal muscle having microtears))) comprises between 0.1 mg-200 mg (e.g., 0.1 to 5000; 0.2 to 4000; 0.3 to 3000; 0.4 to 2500; 0.5 to 2000; 0.6 to 1500; 0.7 to 1000; 1 to 800; 10 to 500; 100 to 450; 200 to 400; 300 to 350; etc.) of poloxamer per kg weight of the subject being treated. In some embodiments, each dose comprises between 0.46 mg to 500 mg of poloxamer per kg weight of the subject being treated. In some embodiments, each dose comprises 0.46 mg of poloxamer per kg weight of the subject being treated. In some embodiments, each dose comprises between 200-400 mg of poloxamer per kg weight of the subject being treated. In some embodiments, each dose comprises between 400-500 mg of poloxamer per kg weight of the subject being treated. In some embodiments, each dose comprises 500-2000 mg of poloxamer per kg weight of the subject being treated. In some embodiments, each dose comprises less than 100 mg of poloxamer per kg weight of the subject being treated. In some embodiments, each dose comprises more than 2000 mg of poloxamer per kg weight of the subject being treated. In some embodiments, each dose comprises between 400-520 mg of poloxamer per kg weight of the subject being treated. In some embodiments, each dose comprises more between 425-495 mg of poloxamer per kg weight of the subject being treated. In some embodiments, each dose comprises between 450-470 mg of poloxamer per kg weight of the subject being treated. In some embodiments, each dose comprises 460 mg of poloxamer per kg weight of the subject being treated.

The methods are not limited to a particular manner of administration of poloxamer to a subject. Examples of administration include, but are not limited to, intravenous, intraarterial, subcutaneous, intraperitoneal, intramuscular injection or infusion, intrathecal and intraventricular administration.

In some embodiments, the treating and/or preventing decreases susceptibility to calcium overload in the skeletal muscle of the subject. In some embodiments, decreasing susceptibility to calcium overload in skeletal muscle tissue of the subject comprises lowering intracellular $Ca^{+2}$ levels in the skeletal muscle sarcolemma of the subject. In some embodiments, lowering intracellular $Ca^{+2}$ levels in skeletal muscle prevents remodelling or reverses remodelling of skeletal muscle tissue in the subject.

In some embodiments, the composition comprising a poloxamer is co-administered with one or more agents useful in treating skeletal muscle deficiencies. Examples of such agents include, but not limited to, streptomyocin, prednisone, deflazacort, azathioprine, cyclosporine, valproic acid, phenylbutyrate, sodium butyrate, M344, suberoylanilide hydroxamic acid, and PCT124, or a combination of these agents.

In certain embodiments, the present invention provides compositions comprising a poloxamer and an agent useful for the treatment of a skeletal muscle contraction force deficit. In some embodiments, the agent useful for the treatment of a skeletal muscle contraction force deficit is selected from the group consisting of streptomyocin, prednisone, deflazacort, azathioprine, cyclosporine, valproic acid, phenylbutyrate, sodium butyrate, M344, suberoylanilide hydroxamic acid, and PCT124, or a combination of these agents. In some embodiments, the composition comprises two or more agents useful for the treatment of a skeletal muscle contraction force deficit. The compositions are not limited to a particular type of poloxamer. In some embodiments, the poloxamer is P188, P138, P237, P288, P124, P338, and/or P407. In some embodiments, poloxamines and/or polyglycidols are used instead of, or with, poloxamers. The methods of the present invention are not limited to particular types of skeletal muscle. Examples of skeletal muscle include, but are not limited to, at least one of the following skeletal muscles: gastrocnemius, tibialis posterior, soleus, longus, brevis, gluteus maximus muscle, biceps femoris, semitendinosus, semimembranosus, iliopsoas, quadriceps femoriss, adductor muscles of the hip, levator scapulae, trapezius, rectus abdominis, transversus abdominis, abdominal external oblique muscle, abdominal internal oblique muscle, erector spinae, pectoralis major, biceps brachii, triceps brachii, brachialis, pronator teres, brachioradialis, rhomboids, deltoid, latissimus dorsi, diaphragm and rotator cuff.

In certain embodiments, the present invention provides compositions comprising a poloxamer in contact with a skeletal muscle having a contraction force deficit. In some embodiments, the skeletal muscle having a contraction force deficit is derived from a dystrophin deficient subject. The compositions are not limited to a particular type of poloxamer. In some embodiments, the poloxamer is P188, P138, P237, P288, P124, P338, and/or P407. In some embodiments, poloxamines and/or polyglycidols are used instead of, or with, poloxamers. In some embodiments, the skeletal muscle includes, but is not limited to, at least one of the following skeletal muscles: gastrocnemius, tibialis posterior, soleus, longus, brevis, gluteus maximus muscle, biceps femoris, semitendinosus, semimembranosus, iliopsoas, quadriceps femoriss, adductor muscles of the hip, levator scapulae, trapezius, rectus abdominis, transversus abdominis, abdominal external oblique muscle, abdominal internal oblique muscle, erector spinae, pectoralis major, biceps brachii, triceps brachii, brachialis, pronator teres, brachioradialis, rhomboids, deltoid, latissimus dorsi, diaphragm and rotator cuff.

BRIEF DESCRIPTION OF THE DRAWINGS

FIG. 2 shows lumbrical muscle from the $2^{nd}$ digit of the forepaw of a mouse within experiments conducted during the development of embodiments for the present invention. (A) Muscle is shown alongside a 30G hypodermic needle. (B) Hematoxylin and eosin stained cross-section of a WT lumbrical muscle before isometric contraction protocol. Muscles typically consist of 200-250 fibres and are approximately 300 µm in diameter. (C) mdx muscle before isometric contraction protocol. Dystrophic features include presence of central nuclei and mononuclear cell infiltration. (D) Distal end of an mdx muscle 10 minutes after the isometric contraction protocol. Of all 160 muscle fibres, approximately 10% appear either dark and enlarged (arrows) or devoid of cell matter (asterisks). These abnormalities are indicative of hypercontracted muscle fibres. (E) mdx lumbrical muscle visualized in-vitro along its longitudinal axis after the isometric contraction protocol. Muscle was incubated with Evans Blue Dye and shows the presence of void areas immediately adjacent to hypercontracted regions in the muscle fibres.

DEFINITIONS

As used herein, the term "signs and symptoms of a skeletal muscle deficiency" refers to signs and symptoms associated with a skeletal muscle deficiency (e.g., recognized by simple observation and, when combined with an individual's activity, age, and family history of skeletal muscle deficiency, can lead to an accurate and early diagnosis of a disorder related to skeletal muscle deficiency (e.g., DMD)). Examples of signs and symptoms of a skeletal muscle deficiency include, but are not limited to, a dystrophin-deficient skeletal muscle, skeletal muscle having a contraction force deficit, skeletal muscle having a $Ca^{2+}$ imbalance, and skeletal muscle having microtears. The term "wherein said symptoms are reduced" refers to a qualitative or quantitative reduction in detectable symptoms, including but not limited to improved skeletal muscle contraction force, reduced skeletal muscle microtears, and/or improved skeletal muscle $Ca^{2+}$ balance.

As used herein, the term "at risk for a skeletal muscle deficiency" refers to subjects (e.g., a segment of the world population, or research animals) that have an increased risk (i.e. over the average subject (e.g., person or research animal) for a skeletal muscle deficiency (e.g., dystrophin-deficient skeletal muscle; skeletal muscle having a contraction force deficit; skeletal muscle having a $Ca^{2+}$ imbalance; skeletal muscle having microtears) (e.g., a subject with DMD) and can occur at any age.

As used herein, the term "therapeutic composition comprising a poloxamer" refers to compositions containing a poloxamer (e.g., P188), or combination of poloxamers, used for the treatment of a skeletal muscle deficiency. A therapeutic composition comprising a poloxamer may also comprise one or more other compounds or agents including, but not limited to, streptomyocin, prednisone, deflazacort, azathioprine, cyclosporine, valproic acid, phenylbutyrate, sodium butyrate, M344, suberoylanilide hydroxamic acid, and PCT124, or a combination of these agents, and/or other therapeutic agents, physiologically tolerable liquids, gels, carriers, diluents, excipients, salicylates, immunosuppressants, antibiotics, binders, fillers, preservatives, stabilizing agents, emulsifiers, and buffers.

As used herein, the terms "host," "subject" and "patient" refer to any animal, including but not limited to, human and non-human animals (e.g. rodents), non-human primates, ovines, bovines, ruminants, lagomorphs, porcines, caprines, equines, canines, felines, etc.), that is studied, analyzed, tested, diagnosed or treated (e.g. administered therapeutically or prophylactically a composition comprising a poloxamer of the present invention). The terms "host," "subject" and "patient" are used interchangeably, unless indicated otherwise herein.

As used herein, the terms "therapeutically effective amount" and "effective amount" when used in reference to a composition comprising a poloxamer of the present invention refer to an amount (e.g., a dosage level) sufficient to effect beneficial or desired results (e.g., that are effective at treating or preventing a skeletal muscle deficiency). An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs).

As used herein, the terms "co-administration" and "co-administering" refer to the administration of at least two agent(s) (e.g., a composition comprising a poloxamer and one or more other agents—e.g., prednisone, streptomyocin) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of a skeletal muscle deficiency. An agent that causes an improvement in any parameter associated with disease when used in screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or dysfunction (e.g., muscle injury, DMD and/or a skeletal muscle deficiency) as well as those in which a disease and/or dysfunction is to be prevented (e.g., using a prophylactic treatment of the present invention).

As used herein, the term "at risk for disease or dysfunction" refers to a subject (e.g., a human) that is predisposed to experiencing a particular disease or dysfunction. This predisposition may be genetic (e.g., a particular genetic tendency to experience the disease, such as heritable disorders), or due to other factors (e.g., environmental conditions, hypertension, activity level, metabolic syndrome, etc.). Thus, it is not intended that the present invention be limited to any particular risk, nor is it intended that the present invention be limited to any particular type of disorder or dysfunction related to skeletal muscle deficiencies (e.g., DMD).

As used herein, the term "suffering from disease or dysfunction" refers to a subject (e.g., a human) that is experiencing a particular disease or dysfunction. It is not intended that the present invention be limited to any particular signs or symptoms, nor disease. Thus, it is intended that the present invention encompass subjects that are experiencing any range of disease or dysfunction wherein the subject exhibits at least some of the indicia (e.g., signs and symptoms) associated with the particular disease or dysfunction.

The terms "compound" and "agents" refer to any chemical entity, pharmaceutical, drug, and the like that can be used to treat or prevent a disease, illness, sickness, or disorder of bodily function. Compounds comprise both known and potential therapeutic compounds. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease or dysfunction.

DETAILED DESCRIPTION OF THE INVENTION

Skeletal muscle is a type of striated muscle, usually attached to the skeleton. Skeletal muscles are used to create movement, by applying force to bones and joints; via contraction. They generally contract voluntarily (via somatic nerve stimulation), although they can contract involuntarily through reflexes.

Muscle cells (also called fibers) have an elongated, cylindrical shape, and are multinucleated (in vertebrates and flies). The nuclei of these muscles are located in the peripheral aspect of the cell, just under the plasma membrane, which vacates the central part of the muscle fiber for myofibrils.

Skeletal muscles have one end (the "origin") attached to a bone closer to the centre of the body's axis and this is often but not always a relatively stationary bone (such as the scapula) and the other end (the "insertion") is attached across a joint to another bone further from the body's axis (such as the humerus). Contraction of the muscle causes the bones to rotate about the joint and the bones to move relative to one another (e.g., such as lifting of the upper arm in the case of the origin and insertion described here).

Approximately 1 in every 3500 males is affected with Duchenne Muscular Dystrophy (DMD) while Becker Muscular Dystrophy (BMD) is less common affecting approximately 1 in every 30,000 males. Both diseases are the result of mutations in the gene located on the X chromosome, at Xp21.1 that encodes dystrophin. In DMD, dystrophin is absent while in BMD it is either reduced or abnormal in size. Dystrophin is a structural protein that participates in cellular organization in muscle cells and promotes both myofibrillular and sarcolemma (muscle cell membrane) stability (see, e.g., Kaprielian and Severs, 2000 Heart Failure Reviews 5: 221-238).

Discovered in 1984, the mdx mouse (see, e.g., Bulfield G, et al., (1984) Proc Natl Acad Sci USA 81, 1189-1192) lacks dystrophin and is an important model for studying the effects of dystrophin deficiency. Studies performed on muscle tissue from the mdx mouse have documented impairments in structure and function (see, e.g., Lynch G S, et al., (2001) J Physiol 535, 591-600; Head S I, et al., (1992) Proc Biol Sci 248, 163-169) that include a high degree of susceptibility to contraction-induced force deficits associated with lengthening contractions (see, e.g, Li S, et al., (2006) Hum Mol Genet 15, 1610-1622). Depending on the type of muscle fibre and severity of the injury-producing protocol, dystrophic skeletal muscles sustain a loss in force that is 2 to 7 times greater than muscles of wild-type (WT) mice exposed to the same lengthening contraction protocol (see, e.g, Li S, et al., (2006) Hum Mol Genet 15, 1610-1622). In addition, dystrophic muscles have a sarcolemma that is more permeable to extracellular ions and membrane impermeable dyes (see, e.g., Yeung E W, et al., (2005) J Physiol 562, 367-380; Vandebrouck C, et al., (2002) J Cell Biol 158, 1089-1096; Petrof B J (2002) Am J Phys Med Rehabil 81, S162-S174). Potential pathways responsible for allowing the influx of normally-excluded extracellular constituents into dystrophic muscle fibres include micromembrane tears (see, e.g., Petrof B J (2002) Am J Phys Med Rehabil 81, S162-S174) and malfunctioning ion channels (see, e.g., Yeung E W, et al., (2005) J Physiol 562, 367-380; Vandebrouck C, et al., (2002) J Cell Biol 158, 1089-1096). These pathways allow extracellular calcium to enter muscle fibres and result in an elevated intracellular concentration of calcium. The elevated calcium concentration is deleterious to muscle structure and function through a variety of calcium-dependent mechanisms (see, e.g., Lamb G D, et al., (1995) J Physiol 489 (Pt 2), 349-362; Verburg E, et al., (2005) J Physiol 564, 775-790). Despite a general acceptance that membranes of dystrophic skeletal muscles are "leakier" than those of WT mice (see, e.g., Yeung E W, et al., (2005) J Physiol 562, 367-380; Vandebrouck C, et al., (2002) J Cell Biol 158, 1089-1096; Petrof B J (2002) Am J Phys Med Rehabil 81, S162-S174), the relative contributions of micromembrane tears and dysfunctional ion channels to the contraction-induced force deficit have not been established.

Streptomycin is an inhibitor of stretch-activated channels (SAC) (see, e.g., Sokabe M, et al., (1993) Ann N Y Acad Sci 707, 417-420) that reduces the magnitude of contraction-induced injury in dystrophic muscles (see, e.g., Yeung E W, et al., (2005) J Physiol 562, 367-380). Poloxamer 188 (P188) is an 8.4 kDa amphiphilic polymer that effectively patches disrupted membranes in neurons (see, e.g., Marks J D, et al., (2001) FASEB J 15, 1107-1109) and cardiac myocytes (see, e.g., Yasuda S, et al., (2005) Nature 436, 1025-1029). P188 also enhances recovery of skeletal muscle (see, e.g., Lee R C, et al., (1992) Proc Natl Acad Sci USA 89, 4524-4528), fibroblasts (see, e.g., Merchant F A, et al., (1998) J Surg Res 74, 131-140) and the spinal cord (see, e.g., Borgens R B, et al., (2004) J Neurosci Res 76, 141-154) from a variety of injury-inducing protocols.

Experiments conducted during the course of development of embodiments for the present invention investigated, for example, the use of streptomycin and poloxamers, the extent to which mechanosensitive channels and micromembrane tears are responsible for the increased susceptibility of dystrophic muscles to contraction-induced injury. For example, lumbrical (LMB) muscles were treated with streptomycin or Poloxamer 188 and subsequently administered an isometric contraction protocol in-vitro that produced a force deficit in dystrophic muscles. It was shown that poloxamers are effective in reducing the contraction-induced force deficit in a whole mdx skeletal muscle. It was shown that treatment of mdx muscles with streptomycin was equally effective in reducing the contraction-induced force deficit, but likely via, for example, a mechanism different from that of poloxamers. These results were unexpected. Indeed, previous research indicated that poloxamers failed to prevent exercise induced membrane breakdown in mdx skeletal muscle fibers (see, e.g., Quinlan, J. G., et al., (2006) Neuromuscul. Disord. 16(12) 855-864).

Accordingly, the present invention provides novel insights into the pathogenesis of skeletal muscle disorders (e.g., DMD, and related disorders) and compositions and methods for the treatment and prevention of the same and for research uses. In some embodiments, the present invention provides methods of treating, for example, dystrophin-deficient skeletal muscle, skeletal muscle having a contraction force deficit, skeletal muscle having a $Ca^{2+}$ imbalance, and/or skeletal muscle having microtears (e.g., caused by DMD, caused by exercise-induced injury, or other causes) with a membrane sealant poloxamer (e.g., poloxamer 188-P188). In some embodiments, treatment with a poloxamer (e.g., P188) reverses skeletal muscle contraction force deficit in dystrophin-deficient skeletal muscles (see, e.g., Examples I and II). In some embodiments, treatment with a poloxamer is used in the treatment of DMD. In some embodiments, the invention provides methods of protecting skeletal muscle cells and subjects (e.g., humans, non-human mammals, etc.) from developing dystrophin-deficient skeletal muscle, skeletal muscle having a contraction force deficit, skeletal muscle having a $Ca^{2+}$ imbalance, and/or skeletal muscle having microtears, via administering to the subject a poloxamer (e.g., P188). In further embodiments, the invention provides treatments for a dystrophin deficiency disorder (e.g., DMD) in a subject comprising administering (e.g., intravenous (IV) administration) to the subject a composition comprising a poloxamer (e.g., P188). In some embodiments, the subject is any subject having or susceptible to skeletal muscle induced injury. Although an understanding of the mechanism is not necessary to practice the present invention and the present invention is not limited to any particular mechanism of action, in some embodiments, administration of a composition comprising a poloxamer (e.g., P188) produces improvements (e.g., immediate and/or sustained) in skeletal muscle function (e.g., skeletal muscle contraction force) due to a sealing of skeletal muscle micromembrane tears so as to prevent, for example, the entry of extracellular calcium into muscle fibers.

Current therapeutic paradigms for DMD are focused on the expression of dystrophin, through exon skipping or viral transduction of truncated dystrophin, or other genes (e.g., utrophin or dysferlin) that limit the consequences of dystrophin deficiency (See, e.g., Gregorevic, et al., Nat Med 10, 828-34 (2004); Squire et al., Hum Mol Genet 11, 3333-44 (2002); Torrente et al., J Clin Invest 114, 182-95 (2004); Goyenvalle et al., Science 306, 1796-9 (2004)). These strategies are promising but are challenging due to the requisite targeting of all striated muscle in the body. The present invention provides a comparatively simple chemical-based alternative for treating DMD comprising administering to a subject with DMD a composition comprising a poloxamer. Although an understanding of the mechanism is not necessary to practice the present invention and the present invention is not limited to any particular mechanism of action, in some embodiments, administration of a poloxamer results in acute membrane stabilization and/or repair.

As demonstrated herein (e.g., in mouse models of DMD; See Examples I and II), administration of a poloxamer provides ready and immediate improvement for skeletal muscle. Currently, P188 is in phase III clinical trials for the treatment of vaso-occlusive crisis in sickle-cell anemia patients, having recently demonstrated the safety and non-toxicity of P188 in humans (See, e.g., Adams-Graves et al., Blood 90, 2041-6 (1997)). However, unlike the episodic course of sickle-cell anemia, DMD is a progressive disease, and effective poloxamer therapy, in some embodiments, utilizes chronic intravascular administration. Thus, the present invention utilizes membrane sealing poloxamers that represent a new class of therapeutic agents for preventing or limiting progressive damage to DMD, and for treating skeletal muscle deficiencies (e.g., dystrophin-deficient skeletal muscle; skeletal muscle having a contraction force deficit; skeletal muscle having a $Ca^{2+}$ imbalance; skeletal muscle having microtears).

The present invention is not limited to any particular poloxamer for use in stabilizing the membrane of skeletal muscles in subjects (e.g., thereby increasing cellular compliance and improving skeletal muscle function). In some preferred embodiments, P188 is used (e.g., in a composition (e.g., pharmaceutical composition) of the present invention). The present invention is not limited to use of P188. Indeed, any poloxamer that possesses similar characteristics and traits (e.g., biological effects) with those of P188 find use in the present invention including, but not limited to, P138, P237, P288, P124, P338, and P407.

P188 is one of a family of poloxamer molecules originally developed by BASF in the 1950s. It is a nonionic triblock co-polymer made of poly (ethylene oxide)$_{80}$-poly (propylene oxide)$_{30}$-poly (ethylene oxide)$_{80}$ (molecular mass≈8.4 Kda). The molecule has several names including PLURONIC F68, RheothRx, and FLOCOR.

Figure 1:
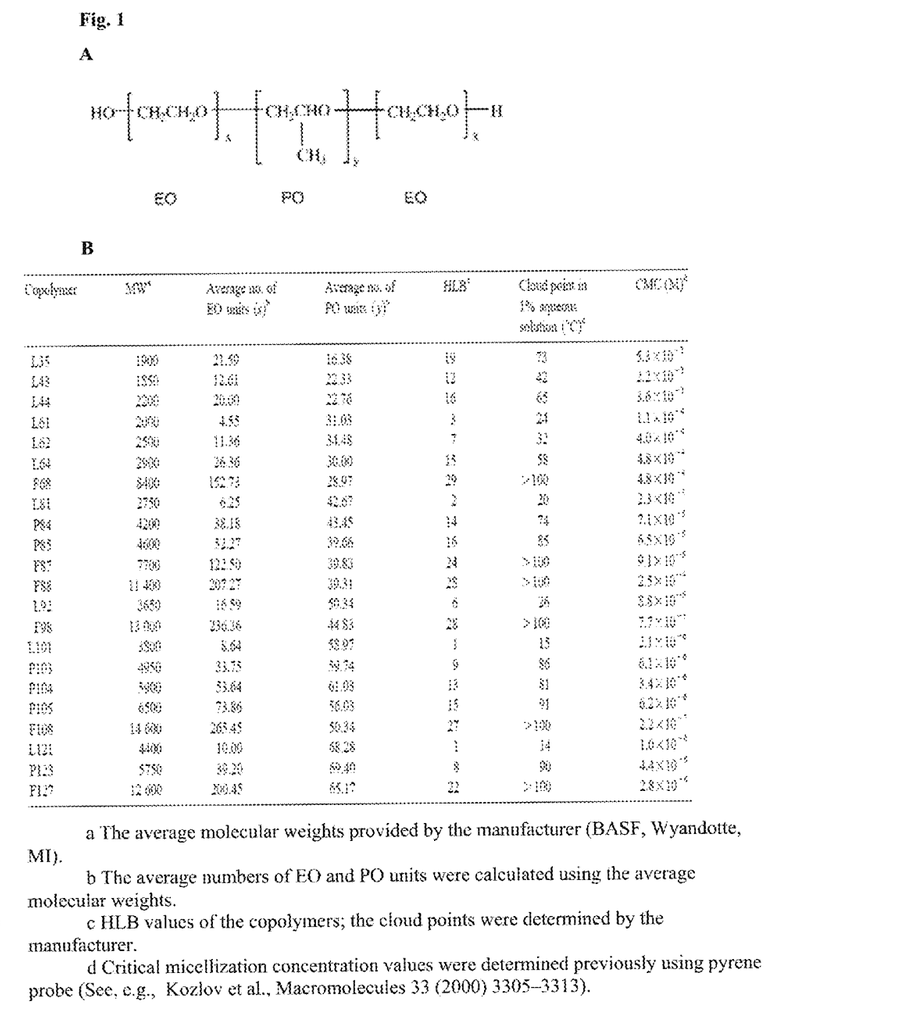
FIG. 1 shows (A) the backbone structure of a poloxamer and (B) examples of commercially available poloxamers useful in compositions and methods of the present invention.

Poloxamers (also termed PLURONIC block polymers, available from BASF Corp., Wyandotte, Mich.) generally comprise ethylene oxide (EO) and propylene oxide (PO) blocks arranged in a basic A-B-A structure: EO-PO-EO. This arrangement results in an amphiphilic copolymer, in which the number of hydrophilic EO$_{(x)}$ and hydrophobic PO$_{(y)}$ units can be altered (See, e.g., Reeve, pgs. 231-249, in Handbook of Biodegradable Polymers, Harwood Academic Pub., Eds. Domb et al., (1997)). The backbone structure of various poloxamers is shown in FIG. 1A. A list of selected PLURONIC copolymers available from BASF Corp. is shown in FIG. 1B. Copolymers with various x and y values are characterized by distinct hydrophilic-lipophilic balance (HLB). Poloxamers can be synthesized by sequential addition of PO and EO monomers in the presence of an alkaline catalyst, such as sodium or potassium hydroxide (See, e.g., Schmolka, J. Am. Oil Chem. Soc. 54 (1977) 110-116). The reaction is initiated by polymerization of the PO block followed by the growth of EO chains at both ends of the PO block. Anionic polymerization usually produces polymers with a relatively low polydispersity index (M/M).

In some embodiments, a composition comprising a poloxamer of the present invention comprises a purified and/or fractionated poloxamer (e.g., purified and/or fractionated using gel filtration or chromatographic fractionation (See, e.g., Emanuele et al., Expert Opin Investig Drugs. 1998; 7:1193-20, U.S. Pat. Nos. 6,977,045 and 6,761,824). In some embodiments, poloxamers are used that have admixtures (e.g., PO homopolymer and/or block copolymer admixtures) removed. In some embodiments, a poloxamer (e.g., polyoxypropylene/polyoxyethylene copolymer) is used that is optimized for improved biological activity (See, e.g., U.S. Pat. No. 6,747,064). In some embodiments, chemically modified forms of one or more poloxamers are utilized in the compositions and methods of the present invention. Chemical modifications of poloxamers include, but are not limited to, radiolabelling, acetylating, biotinylation, addition of a fluorophore, and other chemical modifications.

A variety of poloxamers can be used in (e.g., in a composition comprising a poloxamer) the present invention that possess similar characteristics and traits (e.g., biological effects) with those of P188 (e.g., based on characteristics described in FIG. 1b). These poloxamers include, but are not limited to, P138, P237, P288, P124, P338, and P407. In some embodiments, a poloxamer with a molecular weight of between 5000 and 9000 daltons is used (e.g., in a composition (e.g., pharmaceutical composition) of the present invention). In some embodiments, a poloxamer with a molecular weight of between 9000 and 12000 daltons is used (e.g., in a composition (e.g., pharmaceutical composition) of the present invention). In some embodiments, a poloxamer with a molecular weight of between 12000 and 15000 daltons is used. A poloxamer with a molecular weight below 5000 or greater than 15000 daltons may also find use in the present invention (e.g., in a composition (e.g., pharmaceutical composition) of the present invention).

In some embodiments, a poloxamer with a polyoxyethylene content greater than 50% is used (e.g., in a composition (e.g., pharmaceutical composition) of the present invention). In some embodiments, a poloxamer with a polyoxyethylene content between 50 and 60% is used. In some embodiments, a poloxamer with a polyoxyethylene content between 60 and 70% is used. Poloxamers with a polyoxyethylene content below 50% and above 70% may also find use in the present invention (e.g., in a composition (e.g., pharmaceutical composition) of the present invention).

Some common biological uses of P188 include use as a stool softener in several commercially available laxatives, as an ingredient in cosmetics and as an emulsifier for pharmaceutical agents. It is a powerful surfactant. P188 has been shown to insert into lipid monolayers (See, e.g., Maskarinec et al., 2002 Biophys. J. 82: 1453-1459). It has many biological effects in vivo including the repair of electrically damaged cell membranes (See, e.g., Lee et al., (1992) Proc. Natl. Acad. Sci. USA 89: 4524-4528), in controlled drug delivery, for sensitizing tumors to chemotherapy (See, e.g., Kabanov et al., Adv Drug Deliv Rev 2002, 54, 759-779), and for delivery of gene therapies, among others. Additionally, P188 was shown to have an effect on blood flow and viscosity as well as platelet adhesiveness. (See, e.g., Grover et al., (1969) Circ. 39 and 40: 1249, (Suppl. I)). It was developed as a therapeutic agent under the name of RheothRx by Glaxo Welcome (See, e.g., Adams-Graves et al., (1997), Blood 90: 2041-2046) and by CytRx under the name of FLOCOR for vaso-occlusive crisis in sickle cell disease and has been in phase III clinical trials (See, e.g., Emanuele, (1998) Expert Opin. Investig. Drugs 7:1193-1200). It was also in Phase III trials to assess thrombolytic activity in patients with acute myocardial infarction (MI) (CORE), with mixed results (Schaer et al., (1996) Circ. 94: 298-307; Chareonthaitawe et al., (2000) Heart 84: 142-148). It has been in Phase II trials as an adjunct to primary percutaneous transluminal coronary angioplasty for acute MI (See, e.g., O'Keefe, et al., 1996 Am. J. Cardiol. 78: 747-750). Thus, the present invention contemplates use of poloxamers (e.g., P138, P237 and P288) that enjoy similar characteristics and biological effects to those of P188 (e.g., to treat and/or prevent skeletal muscle deficiencies (e.g., dystrophin-deficient skeletal muscle; skeletal muscle having a contraction force deficit; skeletal muscle having a $Ca^{2+}$ imbalance; skeletal muscle having microtears).

P188 is safe when given acutely for up to 72 hr (See, e.g., Adams-Graves et al., (1997), Blood 90: 2041-2046) and is well tolerated in children and adults upon repeated exposure (See, e.g., Gibbs and Hagemann, 2004 Ann. Pharmacother. 38: 320-324). The most significant adverse effect in studies with RheothRx was renal dysfunction but this was not seen with the more highly purified form FLOCOR. The most frequently experienced adverse effects were pain, injection site abnormalities and nausea. It has a half-life in plasma of 7.5 hr in rodents and 18 hr in human subjects. Pharmacokinetic studies have shown that <5% of purified poloxamer is metabolized. A single metabolite of higher molecular weight and slower clearance has been detected (See, Gibbs and Hagemann, 2004 Ann. Pharmacother. 38: 320-324). Renal clearance is the primary route of elimination.

The present invention provides that a composition comprising a poloxamer (e.g., P188) can be used as a first-in-class therapy for skeletal muscle deficiencies (e.g., dystrophin-deficient skeletal muscle; skeletal muscle having a contraction force deficit; skeletal muscle having a $Ca^{2+}$ imbalance; skeletal muscle having microtears). In some embodiments, a composition comprising a poloxamer (e.g., P188) provides additive or synergistic benefits when administered with one or more compositions (e.g, pharmaceuticals, drugs, etc.) (e.g., streptomycin) used currently for treating DMD (e.g., prednisone, deflazacort, azathioprine, cyclosporine, valproic acid, phenylbutyrate, sodium butyrate, M344, suberoylanilide hydroxamic acid, and PCT124).

In some embodiments, compositions of the present invention are used to prevent entry of extracellular calcium into skeletal muscle through, for example, sealing of skeletal muscle micromembrane tears. For example, in some embodiments, a composition comprising a poloxamer of the present invention can be used to increase cellular compliance and decrease intracellular $Ca^{+2}$ to control levels in unstable skeletal muscle. Although an understanding of the mechanism is not necessary to practice the present invention and the present invention is not limited to any particular mechanism of action, in some embodiments, treating unstable skeletal muscle with a composition comprising a poloxamer of the present invention (e.g., administrating a composition comprising a poloxamer to skeletal muscle) alters (e.g., neutralizes the detrimental effect, and/or reconstitutes (e.g., repairs)) small tears in the sarcolemma.

The present invention is not limited by the type of skeletal muscle deficiency treated (e.g., dystrophin-deficient skeletal muscle; skeletal muscle having a contraction force deficit; skeletal muscle having a $Ca^{2+}$ imbalance; skeletal muscle having microtears). Indeed, any skeletal muscle comprising undesired entry of extracellular calcium into skeletal muscle through, for example, small tears in the sarcolemma can be treated with the compositions and methods of the present invention. In some embodiments, the small tears in the sarcolemma result from a dystrophin deficiency.

The present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have or are likely to suffer from a skeletal muscle deficiency (e.g., dystrophin-deficient skeletal muscle; skeletal muscle having a contraction force deficit; skeletal muscle having a $Ca^{2+}$ imbalance; skeletal muscle having microtears) (e.g., a subject with DMD). In some embodiments, the subjects are non-human mammals (e.g., pigs, cattle, goats, horses, sheep, or other livestock; or mice, rats, rabbits or other animal commonly used in research settings).

The present invention is not limited to a particular type of skeletal muscle to be treated with a composition of the present invention. There are approximately 639 skeletal muscles in the human body (see, e.g., Gray's Anatomy: The Anatomical Basis of Clinical Practice, 39th edition (2004)), each of which may be treated with the compositions of the present invention. Examples of skeletal muscle having a deficiency (e.g., dystrophin-deficient skeletal muscle; skeletal muscle having a contraction force deficit; skeletal muscle having a $Ca^{2+}$ imbalance; skeletal muscle having microtears) that may be treated with the compositions of the present invention include, but are not limited to, at least one of the following skeletal muscles: gastrocnemius, tibialis posterior, soleus, longus, brevis, gluteus maximus muscle, biceps femoris, semitendinosus, semimembranosus, iliopsoas, quadriceps femoriss, adductor muscles of the hip, levator scapulae, trapezius, rectus abdominis, transversus abdominis, abdominal external oblique muscle, abdominal internal oblique muscle, erector spinae, pectoralis major, biceps brachii, triceps brachii, brachialis, pronator teres, brachioradialis, rhomboids, deltoid, latissimus dorsi, and rotator cuff.

The present invention further provides pharmaceutical compositions (e.g., comprising a poloxamer described herein). A composition comprising a poloxamer of the present invention can be used therapeutically (e.g., to correct skeletal muscle having a contraction force deficit; skeletal muscle having a $Ca^{2+}$ imbalance; skeletal muscle having microtears) or as a prophylactic (e.g., to prevent skeletal muscle having a contraction force deficit; skeletal muscle having a $Ca^{2+}$ imbalance; skeletal muscle having microtears). A composition comprising a poloxamer of the present invention can be administered to a subject via a number of different delivery routes and methods.

In preferred embodiments, a composition comprising a poloxamer of the present invention is administered via intravenous (IV) administration. In some embodiments, a composition of the present invention may be administered one or more times a day for several days. In some embodiments, a composition of the present invention may be administered one or more times a day for more than one week. In some embodiments, a composition of the present invention may be administered one or more times a day for two or more weeks. In some embodiments, a composition of the present invention may be administered one or more times a day for one or more months, two or more months, four or more months, eight or more months, or for more than a year. In preferred embodiments, a composition of the present invention is administered (e.g., via chronic administration (e.g., administered one, two, three or more times a week in a physician's office for a duration (e.g., over a period of weeks, months or years) that is sufficient to improve skeletal muscle contraction (e.g., by lowering and maintaining skeletal muscle calcium levels at normal levels). The present invention is not limited to intravenous administration. Indeed, any method of administration that introduces a composition of the present invention into the vasculature is contemplated to be useful as a delivery means. For example, in some embodiments, a composition of the present invention is administered via parenteral administration. Examples of parenteral administration include intravenous, intraarterial, subcutaneous, intraperitoneal, intramuscular injection or infusion, intrathecal or intraventricular administration.

Compositions and formulations for parenteral, IV, or other route of administration may include sterile aqueous solutions that may also contain buffers, diluents and other suitable additives such as, but not limited to, penetration enhancers, carrier compounds and other pharmaceutically acceptable carriers or excipients.

A composition of the present invention may be formulated for administration by any route, such as intravenous, or other route described herein. In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for IV, parenteral, mucosal, subcutaneous, intramuscular, intraperitoneal, intravenous, oral (e.g., via ingestion) or administration via other routes may be found in Remington: The Science and Practice of Pharmacy, Mack Publishing Company, Easton, Pa., 19th edition, 1995.

In additional preferred embodiments, a composition of the present invention is administered in an amount (e.g., a dose) that is sufficient to improve skeletal muscle contraction (e.g., by lowering and maintaining skeletal muscle calcium levels at normal levels). The present invention is not limited to any particular dose. Indeed, the desired dose may vary depending upon the subject being treated (e.g., the age, health status, and type and/or degree of skeletal muscle deficiency being treated).

In some embodiments, it is expected that each dose (e.g., of a composition comprising a poloxamer (e.g., administered to a subject to prevent or treat a skeletal muscle deficiency (e.g., dystrophin-deficient skeletal muscle; skeletal muscle having a contraction force deficit; skeletal muscle having a $Ca^{2+}$ imbalance; skeletal muscle having microtears))) comprises between 100-200 mg of poloxamer per kg weight of the subject being treated. In some embodiments, each dose comprises between 200-400 mg of poloxamer per kg weight of the subject being treated. In some embodiments, each dose comprises between 400-500 mg of poloxamer per kg weight of the subject being treated. In some embodiments, each dose comprises 500-2000 mg of poloxamer per kg weight of the subject being treated. In some embodiments, each dose comprises less than 100 mg of poloxamer per kg weight of the subject being treated. In some embodiments, each dose comprises more than 2000 mg of poloxamer per kg weight of the subject being treated. In some embodiments, each dose comprises between 400-520 mg of poloxamer per kg weight of the subject being treated. In some embodiments, each dose comprises more between 425-495 mg of poloxamer per kg weight of the subject being treated. In some embodiments, each dose comprises between 450-470 mg of poloxamer per kg weight of the subject being treated. In some embodiments, each dose comprises 460 mg of poloxamer per kg weight of the subject being treated. An optimal amount for a particular administration can be ascertained by standard studies involving observation of diastolic function and other biological responses (e.g., blood oxygen saturation) in subjects.

In some embodiments, it is expected that each dose (e.g., of a composition comprising a poloxamer that is administered to a subject (e.g., a human subject)) is by weight 30% poloxamer. However, a dose may comprise more or less than this amount of poloxamer. For example, in some embodiments, a dose may comprise between 30-40% poloxamer by weight. In some embodiments, a dose may comprise between 40-50% w/w poloxamer. In some embodiments, a dose may comprise 50-60% w/w poloxamer. In some embodiments, a dose may comprise greater than 60% poloxamer by weight.

In some embodiments, pharmaceutical preparations comprising a poloxamer are formulated in dosage unit form for ease of administration and uniformity of dosage. Dosage unit form, as used herein, refers to a physically discrete unit of the pharmaceutical preparation appropriate for the subject undergoing treatment (e.g., administration of a composition of the present invention). Each dosage should contain a quantity of the compositions comprising a poloxamer calculated to produce the desired response (e.g., improved skeletal muscle function). Procedures for determining the appropriate dosage unit, in addition to being described herein, are well known to those skilled in the art.

Dosage units may be proportionately increased or decreased based on several factors including, but not limited to, the weight, age, and health status of the subject. In addition, dosage units may be increased or decreased based on the response of the subject to the treatment (e.g., amount of skeletal muscle contraction force deficit).

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the poloxamer of the formulation.

The present invention also includes methods involving co-administration of a composition comprising a poloxamer with one or more additional active agents (e.g., agents that are known in the art for treating or preventing skeletal muscle deficiencies). Indeed, it is a further aspect of this invention to provide methods for enhancing prior art treatment methods and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered can be any of the well-known agents in the art, including, but not limited to, those that are currently in clinical use.

It is contemplated that the administration of a composition comprising a poloxamer may be co-administered with one or more known therapeutic agents for treating skeletal muscle deficiencies. For example, agents that are known in the art for treating skeletal muscle deficiencies (e.g., dystrophin-deficient skeletal muscle; skeletal muscle having a contraction force deficit; skeletal muscle having a $Ca^{2+}$ imbalance; skeletal muscle having microtears) include, but are not limited to, streptomyocin, corticosteroids (e.g., prednisone, deflazacort), immunosupressive agents (e.g., azathioprine, cyclosporine), valproic acid, phenylbutyrate, sodium butyrate, M344 (a benzamide and histone deacetylase [HDAC] inhibitor), suberoylanilide hydroxamic acid (SAHA), and PTC124 (PTC Therapeutics, Inc, South Plainfield, N.J.). PCT124 is an oxadiazole compound that, when taken orally, can override nonsense stop translation signals induced by the dystrophin gene mutation such that the protein produced is the full-length protein (see, e.g., Hamed S A (2006) Drugs November; 9(11): 783-9) (PTC124 is currently in phase II clinical trials for patients with Duchenne MD and cystic fibrosis).

EXPERIMENTAL

The following examples are provided in order to demonstrate and further illustrate certain preferred embodiments and aspects of the present invention and are not to be construed as limiting the scope thereof.

Animals.

Specific-pathogen-free male mdx mice (C57BL/10ScSn-mdx stock #001801) 2-3 months of age and wild type (WT) C57BL/10 mice 2-5 months of age were obtained from the Jackson Laboratory (Bar Harbor, Me.). Mice were housed in a specific-pathogen-free barrier facility. All experimental procedures were in accordance with the *Guide for the Care and Use of Laboratory Animals* [DHHS Publication No. 85-23 (NIH), Revised 1985, Office of Science and Health Reports, Bethesda, Md. 20892].

Operative Procedure.

Mice were anesthetized with an intraperitoneal injection of Avertin (tribromoethanol 400 mg/kg). Supplemental doses of Avertin were administered as required to keep the mouse unresponsive to tactile stimuli. The front paws of the mouse were severed and the LMB muscles dissected free from the second digit. The LMB muscles were selected for their extremely small size that ensured all fibres were accessible to externally applied compounds. Based on physical dimensions, LMB muscle mass was estimated to be approximately 0.7 mg. Dissections were performed in a chilled bathing solution, composition in mM: 137 NaCl, 11.9 $NaHCO_3$, 5.0 KCl, 1.8 $CaCl_2$, 0.5 $MgCl_2$, 0.4 $NaH_2PO_4$. The isolated LMB muscle was mounted horizontally in a custom-fabricated chamber with the distal tendon attached to a force transducer (Aurora Scientific, Inc., modified Model 400A) and the proximal tendon attached to a servomotor (Aurora Scientific, Inc., Model 318B) by ties composed of 10-0 monofilament nylon suture. Bath temperature was maintained at 25° C. and the chamber was perfused continuously with Tyrode solution (composition in mM: 121 NaCl, 24 $NaHCO_3$, 5.0 KCl, 1.8 $CaCl_2$, 0.5 $MgCl_2$, 0.4 $NaH_2PO_4$) maintained at pH 7.3 by bubbling with a 95%/5% $O_2/CO_2$ mixture.

Protocol for Inducing Injury.

Muscles were stimulated electrically by current passed between two platinum electrodes. The constant-current stimulation pulses were 0.5 ms in duration and their magnitude was adjusted to elicit a maximum twitch response. Optimum length ($L_o$) of the muscle was determined by adjusting its length until maximum twitch force was attained. To achieve a maximum isometric tetanic contraction, the muscle was stimulated using a train of pulses at a frequency of 220 pulses per second and with alternating pulse polarity. The protocol used to induce the force deficit consisted of 20 isometric contractions, each lasting 1 second and separated by 1 minute. The one minute rest period between contractions was necessary to minimize fatigue and ensure that any decline in the force generating capability of the muscles during and after the 20 contractions was attributable to contraction-induced injury. To facilitate comparisons among groups of muscles that varied in mass, the absolute isometric force of a muscle during each contraction was normalized to the maximum isometric force ($P_o$) produced by the muscle during the 20-contraction protocol.

Treatment Groups.

LMB muscles from WT mice, termed WT muscles, were divided into two groups. One group was exposed to normal Tyrode solution and the other group to a calcium-free Tyrode solution. Muscles from mdx mice, termed mdx muscles, were divided into 5 groups according to their treatment with: (1) P188, (2) streptomycin, (3) P188 and streptomycin, (4) calcium-free Tyrode, or (5) normal Tyrode. Concentrations of P188 (Bayer, N.J.) and streptomycin (Sigma, #S 1277) in Tyrode solution were 1 mM and 200 μM, respectively. For all treatments, muscles were allowed to incubate in the chamber for 15 minutes prior to commencement of the contraction protocol. Pilot experiments performed on WT muscles exposed to P188 (1 mM) or streptomycin (200 μM) indicated that these compounds were not toxic to the muscle when used at these concentrations. For calcium-free experiments, $CaCl_2$ was omitted from the Tyrode solution and $MgCl_2$ was increased to 2.3 mM to maintain the concentration of divalent ions.

The force deficit that arises from calcium-free experiments have, for example, two possible origins: a contraction-induced force deficit, as well as an "environmental" force deficit caused by prolonged exposure of the muscle to a non-physiological environment. To separate the environmental from the contraction-induced force deficit, it was assumed that the calcium-free environment had an effect that was equally deleterious to both WT and mdx muscles and consequently normalized the force responses of mdx muscles in calcium-free environments to those of WT muscles in the same calcium-free environments. At the end of the contraction protocol, isometric tetanic force of mdx muscles, expressed as a percentage of $P_o$, was divided by the isometric tetanic force of WT muscles, also expressed as a percentage of $P_o$. This normalizing procedure isolated the contraction-induced force deficits, allowing comparisons between the mdx muscles in calcium-free and normal environments.

Statistics.

Data are presented as a mean value±SE. Statistical analysis was performed using either Student's t-test or one-way analysis of variance (ANOVA) with the level of significance set a priori at $P<0.05$. When ANOVA was used and significance detected, the Student-Newman-Keuls post hoc comparison was used to assess pairwise differences.

Example II

This example demonstrates the effectiveness of P188 in reducing contraction-induced force deficit in a whole mdx skeletal muscle, and that treatment of mdx muscles with streptomycin, a stretch-activated channel inhibitor, was equally effective in reducing the contraction-induced force deficit, but likely via a mechanism different from that of P188.

Figure 2:
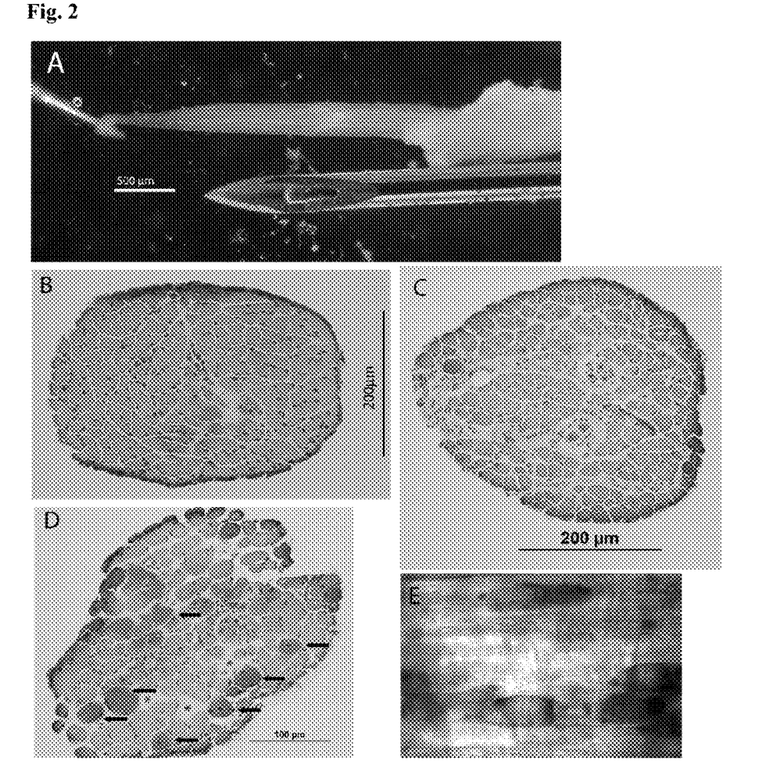
Figure 3:
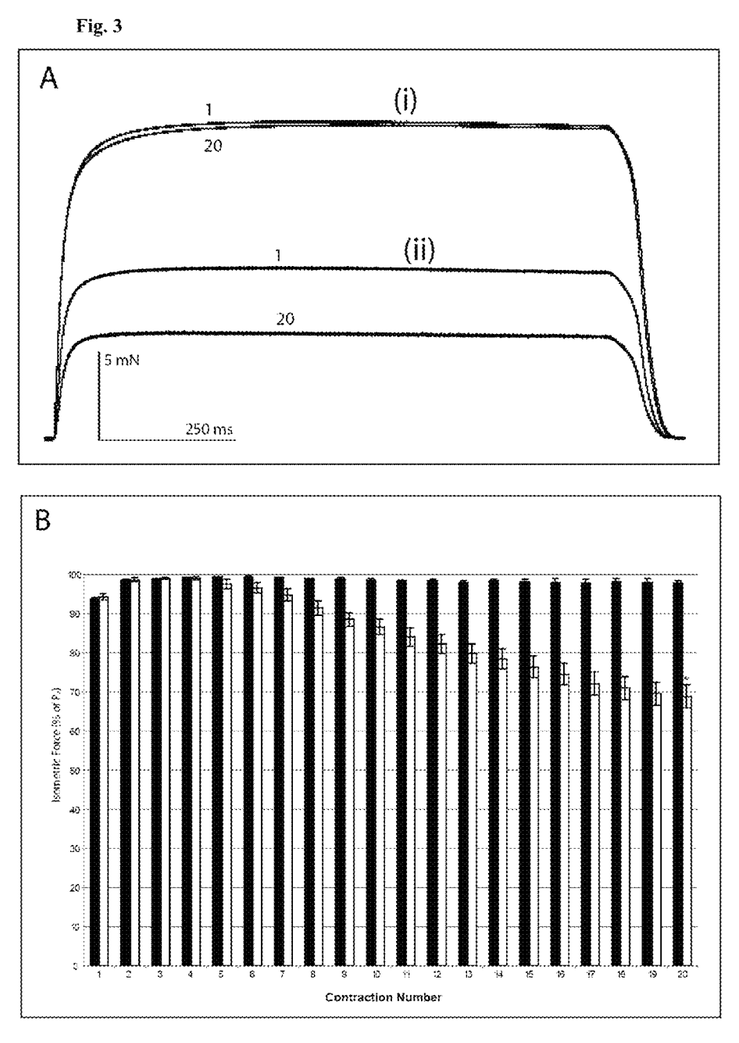
FIG. 3 shows force production of WT and mdx lumbrical muscles within experiments conducted during the development of embodiments for the present invention. (A) Example records of isometric force production: (i) denotes set from a WT mouse, (ii) denotes set from an mdx mouse. For clarity, only records of the first (1) and last (20) isometric contractions are shown. (B) Force production of WT (black bars, n=6) and mdx (white bars, n=8) lumbrical muscles during a protocol of 20 isometric contractions. Data are presented as mean values±SE. Single-tailed Student's t-test was performed only on the 20th contraction. Asterisk indicates a difference from WT group (P<0.05).

Based on the histology of a sub-sample of muscles, LMB muscles were approximately 300 μm in diameter and consisted of 200 to 250 fibres (see, FIG. 2A, B). Cross-sections from mdx muscles displayed typical dystrophic features (see, e.g., Brooks, S V (1998) J Muscle Res Cell Mot 19, 179-187) including areas of mononuclear cell infiltration and the presence of centrally nucleated cells (see, FIG. 2C). The $P_o$ of untreated WT muscles (14.8±0.9 mN, n=6) was greater than the $P_o$ of untreated mdx muscles (10.8±0.4 mM, n=8) ($P<0.05$). At the end of the isometric contraction protocol, WT muscles did not show a force deficit. In contrast, the forces generated by untreated mdx muscles decreased to 69% of $P_o$ by the end of the 20 isometric contraction protocol (see, FIG. 3). This value was unchanged after a 10-minute period of recovery indicating that fatigue was not a contributing factor. After the isometric contraction protocol, histology of mdx muscles revealed the presence of fibres that were enlarged and darkly stained as a result of regions of irreversible hypercontracture along the length of fibres (see, FIG. 2E). In a given cross-section of the muscle, hypercontracture of muscle fibres also resulted in sporadic regions that were devoid of cellular material (see, FIG. 2D). The extent of fibre damage in a given cross-section is, for example, likely to be an underestimate of the fibre damage in a whole muscle; a fibre that appears normal in a cross-section may be damaged in another region along its axis.

Figure 4:
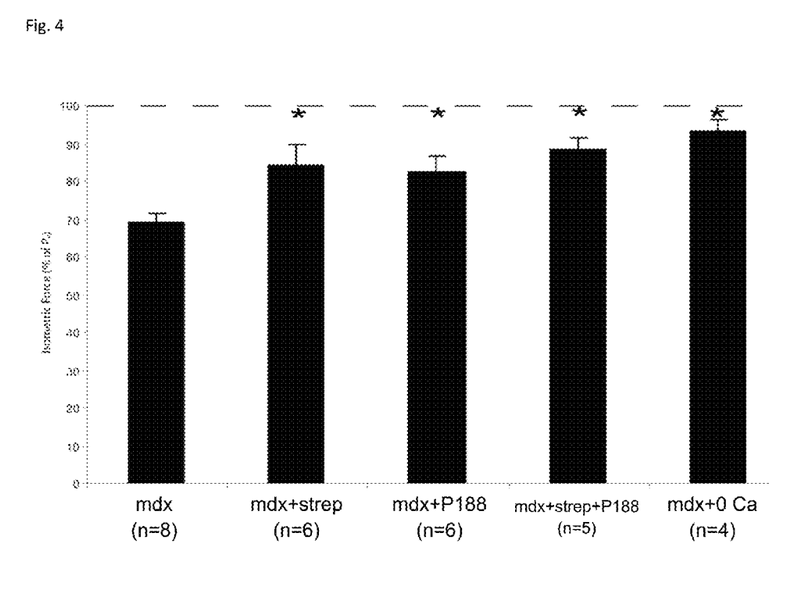
FIG. 4 shows force production of mdx lumbrical muscles at the end of 20 isometric contractions within experiments conducted during the development of embodiments for the present invention. Data are presented as mean values±SE. One way ANOVA was performed followed by Student-Newman-Keuls pairwise comparison between groups. Asterisk indicates a difference from untreated mdx group (P<0.05)

Treatment of mdx muscles with streptomycin, or P188 alone, or with both streptomycin and P188 simultaneously, did not influence the absolute $P_o$. While the absolute $P_o$ was unaffected by treatment, treated muscles showed a reduction in magnitude of the post-protocol force deficit. Compared with untreated mdx muscles, mdx muscles treated with either streptomycin or P188 exhibited an increased ability to generate force at the end of the contraction protocol, with an increase from 69% to 84% and 85% of $P_o$, respectively (see, FIG. 4). When mdx muscles were treated with streptomycin and P188 simultaneously, the post-protocol normalized $P_o$ was not different from treatment with either P188 or streptomycin alone ($P>0.05$) (see, FIG. 4).

In calcium-free Tyrode solution, the absolute $P_o$ of both WT and mdx muscles decreased by approximately 30% to 10.8±0.5 mN (n=3) and 7.2±1.3 mN (n=4), respectively. The decline in the absolute $P_o$ of both WT and mdx muscles were likely caused by the non-physiological calcium-free extracellular environment. When normalized to WT muscles in calcium-free environments, mdx muscles in calcium-free environments generated forces that were 92% of $P_o$, a value that was not different from muscles treated with streptomycin and/or P188 ($P<0.05$) (see, FIG. 4).

By treating mdx muscles with P188 and streptomycin, either separately or simultaneously, a reduction in the force deficit compared with untreated mdx muscles was observed. When the isometric contraction protocol was carried out in a calcium-free environment, mdx muscles again exhibited a reduced force deficit. These results, coupled with a direct observation of calcium entry into LMB muscles of mdx mice during a similar contraction protocol, suggest, for example, that the influx of extracellular calcium occurs through micromembrane tears and SAC, and plays a significant role in the post-protocol force deficit in mdx muscles. This force deficit likely occurs when, for example, the influx of extracellular calcium into mdx muscle fibres causes sustained regional activation that eventually leads to hypercontraction clots and fibre destruction.

All publications and patents mentioned in the above specification are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of treating or reducing diaphragm skeletal muscle injury or diaphragm skeletal muscle deficiency in a subject comprising administering to a subject in need thereof a composition comprising a therapeutically effective amount of a poloxamer.

2. A methhod of claim 1, wherein said diaphragm skeletal muscle deficiency is a skeletal muscle contraction force deficit.

3. A method of claim 1, wherein said poloxamer is a purified or fractionated poloxamer.

4. A method of claim 1, wherein said subject is a human subject.

5. A method of claim 1, wherein said composition is administered via intravenous administration.

6. A method of claim 1, wherein said subject is a dystrophin deficient subject.

7. A method of claim 6, wherein said subject has Duchene's muscular dystrophy.

8. A method of claim 1, wherein said treating decreases susceptibility to calcium overload in the diaphragm skeletal muscle of said subject.

9. A method of claim 1, wherein said poloxamer is P188.

10. A method of claim 1, wherein said poloxamer is administered at a dosage level of approximately between 0.1-5,000 mg per kg weight of said subject.

11. A method of claim 1, wherein said poloxamer is administered at a dosage level of approximately between 0.46-500 mg per kg weight of said subject.

12. A method of claim 1, wherein said dosage level is 0.1-200 mg per kg weight of said subject.

13. A method of claim 1, wherein said composition comprising a poloxamer is coadministered with one or more agents selected from the group consisting of streptomycin, prednisone, deflazacort, azathioprine, cyclosporine, valproic acid, phenylbutyrate, sodium butyrate, M344, and suberoylanilide hydroxamic acid.

* * * * *